(12) United States Patent
Qin

(10) Patent No.: US 6,963,003 B2
(45) Date of Patent: Nov. 8, 2005

(54) OXYGEN-CONTAINING HETEROCYCLIC FUSED NAPHTHOPYRANS

(75) Inventor: Xuzhi Qin, Hacienda Heights, CA (US)

(73) Assignee: Vision-Ease Lane, Ramsey, MN (US)

( * ) Notice: Subject to any disclaimer, the term of this patent is extended or adjusted under 35 U.S.C. 154(b) by 93 days.

(21) Appl. No.: 10/694,111

(22) Filed: Oct. 27, 2003

(65) Prior Publication Data

US 2004/0215024 A1 Oct. 28, 2004

Related U.S. Application Data

(60) Provisional application No. 60/422,147, filed on Oct. 28, 2002.

(51) Int. Cl.[7] ............................................... C07D 311/78
(52) U.S. Cl. ...................................... 549/383; 549/384
(58) Field of Search .................................. 549/383, 384

(56) References Cited

U.S. PATENT DOCUMENTS

| | | |
|---|---|---|
| 6,630,597 B1 | 7/2003 | Lin et al. |
| 6,686,468 B2 | 2/2004 | Mann et al. |

Primary Examiner—Taofiq Solola
(74) Attorney, Agent, or Firm—Inskeep Ip Group

(57) ABSTRACT

This invention relates to novel naphthopyrans having an oxygen-containing heterocyclic group F annelated on the i, j, or k side of the naphthopyran ring, having certain substituents at the 2, 5, and 6 positions of the naphthopyran ring. These naphthopyrans may have the formula (I) presented below:

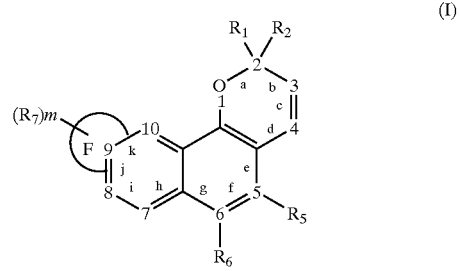

(I)

These compounds (I) have interesting photochromic properties. Also related to this invention are host materials that contain such naphthopyran compounds, and articles such as ophthalmic lenses or other plastic transparencies that incorporate the naphthopyran compounds.

15 Claims, No Drawings

OXYGEN-CONTAINING HETEROCYCLIC FUSED NAPHTHOPYRANS

CROSS REFERENCE TO RELATED APPLICATIONS

This application claims the benefit of U.S. Provisional Application Nos. 60/421,348, filed Oct. 24, 2002 and U.S. Provisional Application No. 60/422,147 filed Oct. 28, 2002, and whose entire contents are hereby incorporated by reference.

BACKGROUND OF THE INVENTION

1. Field of the Invention

The present invention relates to novel naphthopyran-type compounds that have, in particular, photochromic properties. The invention also relates to the use of these photochromic compounds in ophthalmic articles (goggles, lenses and eye-shields, for example). The invention particularly relates to naphthopyrans having an oxygen-containing saturated heterocyclic group fused to the naphthalene ring. These naphthopyrans have two intense absorption bands in the visible light range, and are particularly suitable for use in photochromic articles, such as eyeglass lenses, which have a brown or driver activated color.

2. Background of the Art

Photochromism generally concerns the ability of a compound to reversibly change color under different light conditions. One particular type of photochromic phenomenon concerns the reversible change in color of a compound from an original color to a different color when the compound is exposed to a source of ultraviolet radiation, such as solar radiation or light radiated from a mercury or xenon lamp. The photochromic compound fades to the original color within a period of time after the photochromic compound is isolated from the ultraviolet radiation, such as by placing the compound in a dark room.

Photochromic compounds find applications in various fields, such as for the manufacture of ophthalmic lenses, contact lenses, solar protection glasses, goggles, sun screens, filters, camera optics, photographic apparatus optics or other optical devices and observation devices, glazing, decorative objects, currency elements and even for information storage by optical inscription (coding). For example, photochromic compounds, such as naphthopyrans, are incorporated into plastic ophthalmic lenses to effect color changes in the lenses when the lenses are exposed to particular lighting conditions. Additionally, different photochromic compounds may be blended together to create a color effect that is different from respective color effects of the individual photochromic compounds. As an example, a first photochromic compound that turns orange or red when activated by light and a second photochromic compound that turns blue when activated by light may be blended together to form a photochromic mixture that produces a shade of gray when activated by light.

Amongst the numerous photochromic compounds described in the prior art, naphthopyrans and larger ring systems derived from them received the most intensive investigations due to their suitable properties (fatigue, fading rate, color, temperature dependence) for use in eyeglass lenses. The simplest naphthopyran photochromic compounds are represented by the formula below:

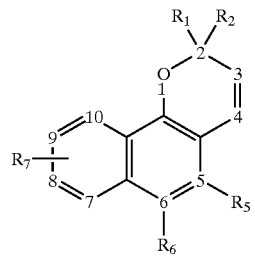

Attempts were made to achieve improvements by using different substituents at various positions, especially on the naphthalene core. The improvements include proper fading rate, desired color, better fatigue, etc. One of the important improvements is for a naphthopyran to provide a blended color hue. As aforementioned, to give eyeglass lenses a neutral gray or brown color, it may necessitate the use of at least two photochromic compounds of different colors, i.e., two separate compounds having distinct maximal absorption wavelengths in the visible region of the electromagnetic spectrum. However, the use of combinations of photochromic compounds imposes other requirements on both the individual photochromic compounds and the groups of photochromic compounds. In particular, the coloration and discoloration kinetics of the (two or more) combined active photochromic compounds must be essentially identical. The same applies for their stability with time, and also for their compatibility with a single plastic or inorganic support.

It is thus highly desirable to obtain photochromic compounds that have a blended color hue provided by two or more distinct absorption bands in the visible region. With such photochromic compounds it is possible to use only one compound for the desired color (e.g., gray or brown), or at least to require minimum amount of complementary color compound.

U.S. Pat. No. 5,645,767 discloses photochromic indeno [2,1-f]naphtho[1,2-b]pyrans having a blue/gray activated color. A blue/gray color will be perceived when there is a major absorption of visible light in the 580–620 nm range (Band B thereafter referring to the longer wavelengths) coupled with a minor absorption in the 420–500 nm range (Band A thereafter referring to the shorter wavelengths).

U.S. Pat. No. 6,096,246 (incorporated by reference) describes naphtho[1,2-b]pyrans having alkoxy groups as substituents at the 7- and 9-positions of the naphthopyran ring. The activated forms of these compounds exhibit two intense absorption bands in the visible light range. It is reported that the optical density of Band A in some cases is higher than the optical density of Band B, but in the majority of cases Band A is of lower optical density than Band B.

U.S. Pat. No. 6,146,554 (incorporated by reference) discloses photochromic indeno[2,1-f]naphtho[1,2-b]pyrans having a green activated color. A greenish color will be perceived when there is a major absorption of visible light in the 580–620 nm range coupled with a major absorption of roughly equal intensity in the 400–480 nm range. U.S. Pat. No. 6,248,264 (incorporated by reference) describes naphtho[1,2-b]pyrans having amino functional groups as substituents at the 7- or 9-positions of the naphthopyran ring. These compounds are disclosed as exhibiting a brown or red/brown activated color. A red/brown color will be perceived when there is a major absorption of visible light in the 420–500 nm range coupled with a minor absorption in the 520–560 nm range.

U.S. Pat. Nos. 6,296,785 and 6,348,6043 (incorporated by reference) disclose indeno[2,1-f]naphtho[1,2-b]pyrans and naphtho[1,2-b]pyrans, respectively, having two adjacent moderate to strong electron donor substituents at the 6 and 7 positions of indeno[2,1-f]naphtho[1,2-b]pyrans and the 8 and 9 positions of naphtho[1,2-b]pyrans. The activated forms of these compounds exhibit two intense absorption bands in the visible light range. In the majority of cases Band A (420–500 nm) is of stronger optical density than Band B (480–620 nm)making them suitable for use in photochromic articles having a brown activated color.

U.S. Pat. No. 6,353,102 (incorporated by reference) describes naphtho[1,2-b]pyrans having carbonyl functional groups as substituents at the 6-position of the naphthopyran ring. These compounds are disclosed as also exhibiting two absorption bands in the visible light range. The relative intensity of the two bands depends on other substituents on the ring.

From the above description, it is apparent that photochromic compounds having two absorption bands can be obtained by selecting certain substituents at the naphthopyran ring, especially at the 6 to 9 positions of the naphtho portion. Although some prior art references teach how to select substituents, it seems that such prior art references are incomplete and do not achieve the formulative results of the present invention.

Therefore, it is an object of this invention to provide novel series of photochromic compounds that exhibit two intense absorption bands in the visible range wherein the relative intensity between Band A and Band B is greater than unity. These photochromic compounds will be especially useful in making brown or driver (red-brown) photochromic articles such as eyeglass lenses with a single compound or minimum use of a complementary color compound.

All publications and patents referred to in this application are hereby incorporated by reference.

DESCRIPTION OF THE INVENTION

An objective of this invention is achieved by preparing a novel family of naphthopyran compounds having a central nucleus of the formula:

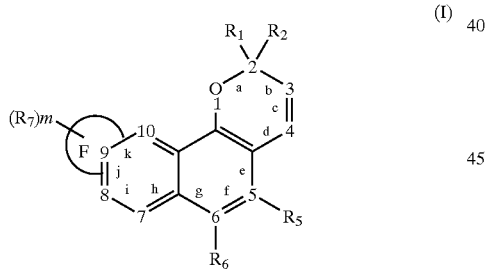

(I)

wherein F is a 5- to 7-member saturated heterocyclic ring group fused to the i or j side of the naphthopyran ring containing one oxygen that is atom directly connected to the 7-, 8- or 9-position;

$R_6$ represents
  i. a C1–C6 alkyl, alkoxy,
  ii. a —C(O)R group, wherein R is selected from hydrogen, hydroxy, alkyl, alkoxy,
  iii. an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:
  iv. a halogen atom (e.g., fluorine, chlorine and bromine),
  v. a hydroxy group,
  vi. a linear or branched alkyl group comprising 1 to 12 carbon atoms,
  vii. a linear or branched alkoxy group comprising 1 to 12 carbon atoms,
  viii. a haloalkyl or haloalkoxy group corresponding to the (C1–C12) alkyl or alkoxy groups above respectively which are substituted with at least one halogen atom, and notably a fluoroalkyl group of this type,
  ix. a linear or branched alkenyl group comprising 2 to 12 carbon atoms, and notably a vinyl group or an allyl group,
  x. an —NH2 group,
  xi. an —NHR8 group, R8 representing a linear or branched alkyl group comprising 1 to 6 carbon atoms,
  xii. a

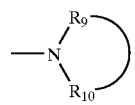

group, in which $R_9$ and $R_{10}$, which are the same or different, independently representing a linear or branched alkyl group comprising 1 to 6 carbon atoms, or representing (together with the nitrogen atom to which they are bound) a 5- to 7-membered ring which can comprise at least one other heteroatom selected from oxygen, sulfur and nitrogen, said nitrogen being optionally substituted with a group that is a linear or branched alkyl group comprising 1 to 6 carbon atoms,
  xiii. a methacryloyl group or an acryloyl group,
  xiv. a polyether, polyamide, polycarbonate, polycarbamate, polyurea or polyester residue;

$R_5$ represents:
  i. a hydroxy,
  ii. a halogen, and notably fluorine, chlorine or bromine,
  iii. a linear or branched alkyl group which comprises 1 to 12 carbon atoms (advantageously 1 to 6 carbon atoms),
  iv. a cycloalkyl group comprising 3 to 12 carbon atoms,
  v. a linear or branched alkoxy group comprising 1 to 12 carbon atoms (most advantageously 1 to 6 carbon atoms),
  vi. a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
  vii. a linear or branched alkenyl or alkynyl group comprising 1–12 carbon atoms, preferably a vinyl or allyl group,
  viii. a linear or branched alkenyloxy or alkynyloxy group comprising 1–12 carbon atoms, preferably an allyloxy group,
  ix. an aryl or heteroaryl group having the same definition as $R_6$ given supra,
  x. an aralkyl or heteroaralkyl group, the alkyl group, which is linear or branched, comprising 1 to 4 carbon atoms, and the aryl and heteroaryl groups having the same definitions as R6 given supra,
  xi. an amine or amide group: —NH$_2$, —NHR$_8$, —CONH$_2$, —CONHR$_8$,

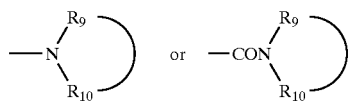

$R_8$, $R_9$, and $R_{10}$ having their respective definitions given above for the amine substituents of the values $R_6$, xii. a —$C(R_{11})_2X$ group, wherein X is —CN, halogen, hydroxy, alkoxy, benzoyloxy, C1–C6 acyloxy, amino, C1–C6 mono-alkamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents, xiii. an —$OCOR_{12}$ or —$COOR_{12}$ group, $R_{12}$ representing a straight or branched alkyl group comprising 1 to 6 carbon atoms, or a cycloalkyl group comprising 3 to 7 carbon atoms, or a phenyl group, optionally substituted with at least one of the substituents listed above within the values in the definitions of $R_6$, xiv. a methacryloyl group or an acryloyl group, an epoxy group having the formula,

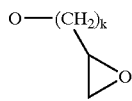

in which k=1, 2 or 3, xv. a polyether, polyamide, polycarbonate, polycarbamate, polyurea or polyester residue;

$R_1$ and $R_2$, which are identical or different, independently represent:
i. a hydrogen,
ii. a linear or branched alkyl group which comprises 1 to 12 carbon atoms (with or without substitution),
iii. a cycloalkyl group which comprises 3 to 12 carbon atoms,
iv. an aryl or heteroaryl group as $R_6$ defined supra,
v. an aralkyl or heteroaralkyl group, the alkyl group, which is linear or branched, comprising 1 to 4 carbon atoms and the aryl and heteroaryl groups having the definitions given above, or
vi. the two substituents R1 and R2 together forming ring group such as those represented by an adamantyl, norbornyl, fluorenylidene, 5,5- or 10,10-di(C1–C6)alkylanthracenylidene, 5 (or 10)-(C1–C6)alkyl-5 (or 10)-OH (or $OR_{15}$)anthracenylidene or spiro(C5–C6) cycloalkylanthracenylidene ring group; said ring group being optionally substituted with at least one of the substituents listed above in the definitions for $R_1$, $R_2$; said ring group being optionally substituted with two adjacent groups that form a 5- to 6-member aromatic or non-aromatic ring which can comprise at least one heteroatom selected from oxygen, sulfur, and nitrogen;

each $R_7$ group can be the same or different, independently representing
i. a hydrogen,
ii. a linear, branched, or cyclic alkyl group,
iii. a linear, branched, or cyclic alkoxy group,
iv. a linear or branched alkenyl or alkynyl group,
v. a linear or branched alkenyloxy or alkynyloxy group,
vi. an aryl or heteroaryl group having the same definition as that given supra for $R_6$, vii. two of the $R_7$ groups, which are adjacent or bonded to the same carbon atom in the group F, form a 5- to 7-membered non-aromatic ring which may comprise at least one hetroatom selected from the group consisting of oxygen, sulfur, and nitrogen, and viii. m is an integer of 0 to 6.

The term "group" has established meanings according to the practice of the present invention. Where the term "group" is used, the chemical unit described is intended to include and allow for substituents consistent with the primary chemical unit. For example, where the term alkyl group is used, that term is intended to include classic alkyl materials such as methyl, ethyl, propyl, butyl, hexyl, octyl, iso-octyl, dodecyl, cyclohexyl and the like, and is also intended to include alkyl units with substitution thereon consistent with the underlying nature of an alkyl unit, such as hydroxymethyl, bromoethyl, dichloropropyl, 1,2,3,4-tetrachlotobutyl, omega-cyanohexyl and the like. Where the term "alkyl moiety" is used, no substitution is allowed.

Where the term 'group' is used in the practice of the present invention, those terms refer to the capability of the structure to have substitution, or no substitution on the chemical unit. The term 'group' refers to any chemical structure, while the term 'central nucleus' refers specifically to a ring structure as the core chemical moiety. For example, an 'alkyl group' includes unsubstituted n-alkyl, iso-alkyl, methyl ethyl, octyly, iso-octyl, docecyl, and the like, and substituted alkyl such as hydroxymethyl, 1-chloroethyl, 2-cyano-butyl, 3-ethyl-4-hexyl, omega-carboxy-pentyl, and the like. Where the term 'moiety' is used, as in the term alkyl moiety, for example, that term refers to only unsubstituted chemical units. Similarly, where the term 'central nucleus' is used, such as in the central nucleus of a naphthyl, any substituent may be present on the central nucleus of the naphthyl group, such as 1-methyl-, 2-chloro-, 2,4-dimethoxy-, 2,2'-dimethoxy-, and the like. Where the term having a structure of the specific formula is used, no substitution is allowed beyond that of the described formula.

Among the substituents that can be considered for the compounds of formula (I) according to the invention, groups should be considered that comprise and/or form at least one function which can be polymerized and/or crosslinked, which groups are preferably selected from the following list including but not limited to: alkenyl, advantageously vinyl, methacryloyl, acryloyl, acryloxyalkyl, methacryloxyalkyl or epoxy.

Thus, the photochromic compounds according to the invention can be monomers, of different types or not, that can react with each other or with other comonomers to form homopolymers and/or copolymers that bear a photochromic functionality and possess mechanical properties of macromolecules. It follows that one of the objects of the present invention consists of these homopolymers or copolymers comprising (co)monomers and/or of crosslinked compounds, that, at least in part, consist of photochromic compounds (I) according to the invention.

In the same general concept, the above-mentioned compounds (I) can be crosslinking agents that have one or more reactive functions capable of allowing the formation of bridges between chains of polymers of photochromic nature or not. The crosslinked compounds that can be obtained in this manner also are a part of the present invention.

Amongst such compounds according to formula (I), preferred photochromic are those which have the formula below: in which:

m and n are integers of 1 or 2,

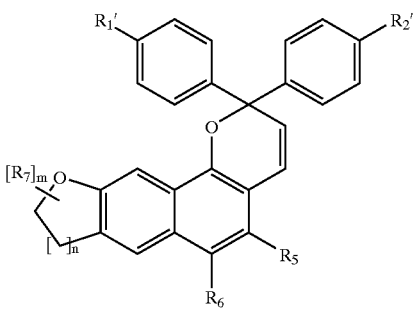

R'$_1$ and R'$_2$, same or different, represent
i. a hydrogen,
ii. a linear, branched, or cyclic alkyl,
iii. an alkyoxy with the alkyl portion being linear, branched, or cyclic,
iv. an unsubstituted, mono- or di-substituted aryl,
v. an aryloxy with the aryl being unsubstituted, mono- or di-substituted;

R$_5$ represents
i. a linear, branched, or cyclic alkyl group,
ii. a linear or branched alkenyl or alkynyl group,
iii. a —C(R$_{11}$)$_2$X group, wherein X is hydroxy, alkoxy, benzoyloxy, C1–C6 acyloxy,
iv. an optionally substituted phenyl or benzyl group,
v. a —COR$_{12}$, or —COOR$_{12}$ group, R$_{12}$ representing a linear, branched, or cyclic alkyl group comprising 1 to 6 carbon atoms;

R$_6$ represents an unsubstituted, mono-, di- or tri-substituted aromatic or hetero-aromatic group selected from phenyl, naphthyl, pyridyl, furanyl, benzofuranyl, thenyl, benzothienyl;

R$_7$ represents
i. a hydrogen,
ii. a linear, branched, or cyclic alkyl group,
iii. a linear, branched, or cyclic alkoxy group,
iv. a linear or branched alkenyl or alkynyl group,
v. a linear or branched alkenyloxy or alkynyloxy group,
vi. an aryl or heteroaryl group having the same definition as that given supra for R$_6$,
vii. two of the R$_7$ groups, which are adjacent or bonded to the same carbon atom in the group F, form a 5- to 7-membered non-aromatic ring which may comprise at least one hetroatom selected from the group consisting of oxygen, sulfur, and nitrogen, and
viii. m is an integer of 0 to 2.

The person skilled in the art will obviously have understood that the branched alkyl, alkoxy, alkenyl, alkenyloxy groups, and cyclic alkyl as defined above, comprise a sufficient number of carbon in order to be branched or cyclic.

These compounds of the invention present particularly advantageous photochromic properties, such as, having strong coloration ability with two intense absorption bands in the visible range. They are particularly useful in making brown or driver colored eyeglass lenses. These compounds are also preferably stable and compatible with matrices made of at least one organic polymer or mineral material (e.g., inert inorganic binder), both in the form included in the matrix and in the form of a coating.

General Synthetic Procedure for Preparation of the Compounds

The compounds of the invention can be obtained by the condensation of a derivative of 1-naphthol that is suitably substituted and a derivative of propargyl alcohol. The condensation can be carried out in organic solvents, particularly non-polar solvents such as toluene, xylene or tetrahydrofuran and, optionally, in the presence of a catalyst, acid catalysts, and especially acid catalysts such as fluorinated organic acid catalysts, p-toluenesulfonic acid, chloroacetic acid or acid aluminic acid):

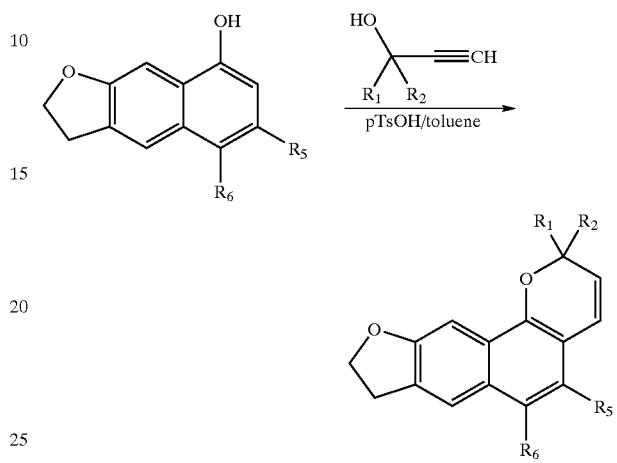

These synthetic routes are classical and have been described in the above-mentioned references of the prior art as well as in U.S. Pat. No. 4,818,096. The propargyl alcohols are either commercially available or easily synthesized by the reaction of lithium acetylide or ethynyl (magnesium bromide) with the corresponding ketones (R$_1$)CO(R$_2$). The ketones are also either commercially available or easily synthesized by the classical methods, for example, the Friedel-Crafts reaction from an acid chloride.

The derivatives of 1-naphthol are obtained by various methods adapted from the literature. Below we give some references on methods that allow the synthesis of the compounds of the invention.

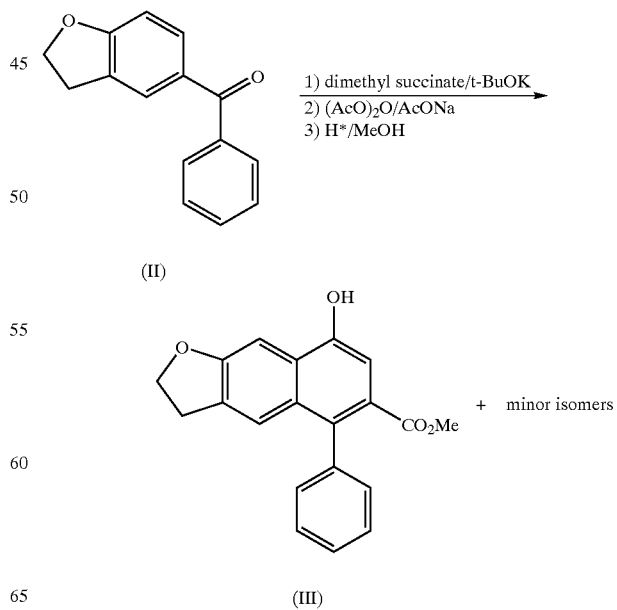

Method 1: Johnson et al. Org. React. 1951, Vol. 6, p. 1.

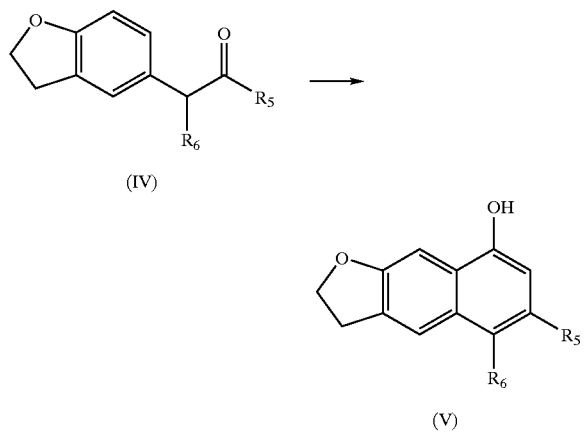

Method 2: U.S. Pat. No. 5,200,116 (Example 2) or U.S. Pat. No. 6,207,084

The starting benzophenone in Method 1 can be prepared by the well-known Friedel-Crafts acylation of dihydrobenzofuran with benzoyl chloride, and the starting ketone in Method 2 can be prepared according to the procedure in U.S. Pat. No. 6,210,608.

To those skilled in the art, the alkoxycarbonyl group in the naphthol (III) can be transformed into a variety of different groups including methyl, hydroxymethyl, benzoyl, alkenyl, etc. For example, they can be used as a photochromic material dispersed in the composition of a polymer matrix. They can also be used in solution.

A photochromic solution can be obtained by dissolving the compound in an organic solvent, such as toluene, dichloromethane, tetrahydrofuran or ethanol. The solutions obtained are generally colorless and transparent. When exposed to sunlight, they develop a strong coloration and they recover the color of this state when placed in an environment with lesser exposure to solar radiation or, in other words, when they are no longer exposed to UV radiation. In general, a very low concentration of products (on the order of 0.01–5% by weight or volume) is sufficient to obtain an intense coloration.

The most interesting applications are those in which the photochrome is dispersed uniformly within or on the surface of a polymer, copolymer or mixture of polymers. The implementation methods that can be considered are of a great variety. Among those known to a person skilled in the art, one can cite, for example, diffusion in the (co)polymer, from a suspension or solution of the photochrome, in a silicone oil, in an aliphatic or aromatic hydrocarbon, in a glycol, or from another polymer matrix. Currently the diffusion is carried out at a temperature of 50–200° C. for a duration of 15 minutes to several hours, depending on the nature of the polymer matrix. Another implementation technique consists in mixing the photochrome in a formulation of polymerizable materials, in depositing this mixture on a surface or in a mold and in then carrying out the polymerization. These implementation techniques and others are described in the article by CRANO et al. "Spiroxazines and

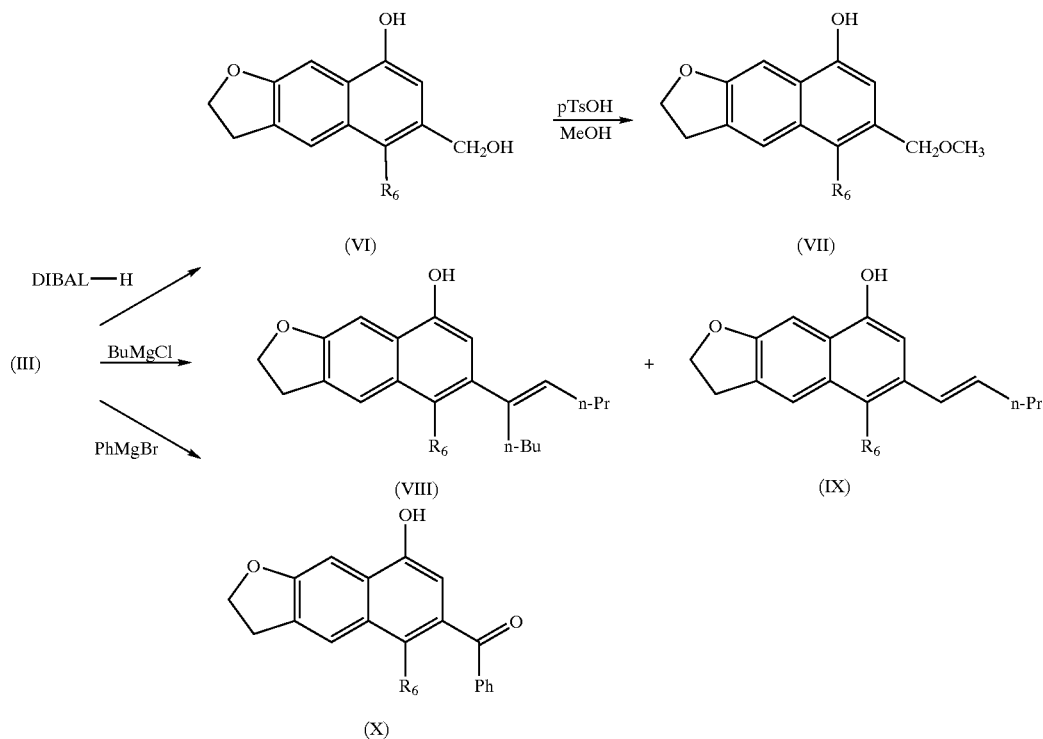

In the reactions, DIBAL-H: diisobutoxyaluminum hydride, pTsOH: p-toluenesulphonic acid, MeOH: methanol.

Regarding the commercial application of compounds according to the present invention, it should be noted that their use in photochromic lenses," published in Applied Photochromic Polymer Systems, Publishers Blackie and Son Ltd., 1992. According to a variant of the invention, it is also possible to consider grafting the photochromes onto (co) polymers. Thus, another aspect of the invention consists of the (co)polymers grafted with at least one of the photochromes described above.

As examples of preferred polymer materials for optical applications of the photochromic compound according to the invention, one can mention the following products including, but not limited to: alkyl, cycloalkyl, aryl or arylalkyl poly(mono-, di-, tri-, tetra)acrylate or poly(mono-, di-, tri-, tetra) methacrylate, optionally halogenated or comprising at least ether and/or ester and/or carbonate and/or carbamate and/or thiocarbamate and/or urea and/or amide group; polystyrene, polycarbonate (e.g., bisphenol A polycarbonate, poly(carbonate of diallyl diethylene glycol), polyepoxy, polyurethane, polythiourethane, polysiloxane, polyacrylonitrile, polyamide, aliphatic or aromatic polyester, vinyl polymers, cellulose acetate, cellulose triacetate, cellulose acetate-propionate or polyvinylbutyral, copolymers of two or more types of monomers or mixtures of the above-mentioned polymers, preferably polycarbonate-polyurethane, poly(meth)acrylate-polyurethane, polystyrene-poly(meth)acrylate or polystyrene-polyacrylonitrile, advantageously a mixture of polyester and/or polycarbonate or poly(meth)acrylate.

In a particularly preferred manner, the photochromic naphthopyrans of the invention are used in polyester or polyether type thermoplastic polyurethanes, two-part polyurethane adhesives.

The quantity of photochrome used in various articles depends on the desired degree of darkening. In particular, it is used in a quantity of 0.01–10 wt % of the total weight of the layer in which the photochrome is included. The photochromic compounds according to the invention can be used alone or in a mixture with other products to form a composition that can be in solid or liquid form, for example, in a solution or in a dispersion, as has already been mentioned above. These compositions, which constitute another object of the invention, can comprise one or more compounds (I) according to the invention and other complementary photochromic compounds which allow the attaining of dark colorations, for example, gray or brown, which the public desires in applications such as ophthalmic or sun-protection eyewear. These additional photochromic compounds can be those known to a person skilled in the art and described in the literature, for example, other naphthopyrans, benzopyrans, chromenes (U.S. Pat. Nos. 3,567,605, 5,238,981, World Patent No. 9,422,850, European Patent No. 562,915), spiropyrans or naphthospiropyrans (U.S. Pat. No. 5,238,981) and spiroxazines (CRANO et al., "Applied Photochromic Polyrmer Systems," Publishers Blackie & Son Ltd., 1992, Chapter 2).

These compositions according to the invention can also comprise:
Non-photochromic dyes allowing the adjustment of the tint, and/or one or more stabilizers, such as, for example, an antioxidant,
and/or one or more anti-UV screens,
and/or one or more anti[free]radical agents,
and/or deactivators that deactivate the states of photochemical excitation.
These additives can enable further improvements in the durability of said compositions.

According to another one of its aspects pertaining to the application of the photochromic compounds (I), the present invention also relates to ophthalmic articles, such as articles of ophthalmic or sun protection eyewear articles, or eye shields comprising at least one compound according to the invention and/or at least one (co)polymer formed, at least in part, of repeating units derived from compounds having formula (I) and/or at least one composition comprising compounds (I) according to the invention, as defined above, and/or at least one matrix, as defined above, made of an organic polymer material or a mineral material or a mineral-organic hybrid material incorporating at least one compound of the invention.

In practice, the articles to which the present invention applies more particularly are photochromic ophthalmic or sun-protection lenses, glass paneling (glasses for buildings, for locomotion devices, automobiles), optical devices, decorative articles, sun-protection articles, information storage, etc.

The present invention will be better understood in the light of the following examples of synthesis and photochromic validation of compounds having the general formula (I). These examples are not intended to be interpreted as limiting the invention, but rather, show specific aspects of the invention within the broad generic scope disclosed.

EXAMPLES

Example 1

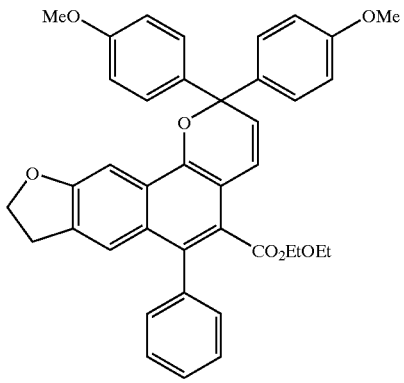

Step 1: To a reaction flask containing 2,3-dihydrobenzofuran (13.5 grams) and benzoyl chloride (16.6 grams) in 170 milliliters (mL) of methylene chloride were added anhydrous aluminum chloride (18.0 grams) under nitrogen blanket over 40 minutes. The reaction temperature was controlled at around 25° C. with an ice/water bath. The reaction mixture was stirred at room temperature overnight. The resulting mixture was poured into 150 mL of ice/water and stirred vigorously for 30 minutes. The organic layer was separated, washed with water, dried over magnesium sulfate. The methylene chloride solvent was removed by rotary evaporation to give 25 grams of thick pink oil. It is used 'as is' in the next step.

Step 2: The product from Step 1 (25 g), dimethyl succinate (21.0 g), and potassium t-butoxide (16.5 g) were mixed in 250 ml of toluene. The mixture was refluxed for 2 hours under nitrogen blanket. After it was cooled to room temperature, 200 ml of water was added and mixed well. The aqueous phase was separated, acidified with 5N HCl, and extracted with 3×100 ml of ethyl acetate. The combined extracts were washed once with water, dried over magnesium sulfate. The solvent was removed under reduced pressure to give 40.5 g of honey-like crude half-ester product. It was known that the crude product contains some aliphatic oil contaminants from the ethyl acetate solvent. It is used without purification.

Step 3: The crude half-ester from Step 2 (40 g) was added to reaction flask containing 180 ml of acetic anhydride and 23 g of anhydrous potassium acetate. The mixture was refluxed for 1.5 hours, cooled, filtered. The solid in the filtration funnel was washed thoroughly with ethyl acetate. The combined filtrate was concentrated to just dry under vacuum. The dark solid was re-dissolved in ethyl acetate and washed with water, dried over magnesium sulfate. The organic solution was concentrated under reduced pressure. The residual was subjected to a silica column with ethyl acetate/hexane 1:4 as elutant. Two main portions were obtained: 8.7 g of light yellow solid, and 36 g of light brown thick oil. An NMR spectrum showed the light yellow solid to have a structure of Compound 1-3-p1: (2,3-dihydro-5-phenyl-6-methoxycarbonyl-8-acetoxy-naphtho[2,3-b]furan). The oil portion contains uncertain amount of Compound 1-3-p1 and its two isomers Compound 1-3-p2 and Compound 1-3-p3, in ethyoxyethanol and methy isoamyl ketone Icontaminates from ethyl acetate solvent.

Step 4: The oil mixture from Step 3 (12 grams) was dissolved in 70 ml of toluene and 10 g of p-toluenesulfonic acid was added. The reaction solution is refluxed for 2 hours, cooled, washed with water, and concentrated to 21 grams of thick oil mixture.

Step 5: The mixture from Step 4 (14.5 grams) was reacted with 2.0 g of 1,1-di(4-methoxyphenyl)-2-propyn-1-ol in 20 ml of toluene in presence of catalytic amount of p-toluenesulfonic acid under reflux for 3 hours. The reaction solution was cooled, concentrated. A silica column with ethyl acetate/hexane 1:4 as eluent provided three photochromic compounds: 450 mg of 1-5-p1, 5 mg of 1-5-p2, and 500 mg of 1-5-p3. Proton NMR confirmed that Compound 1-5-p2 has the molecular structure of this example.

Comparative Example 1

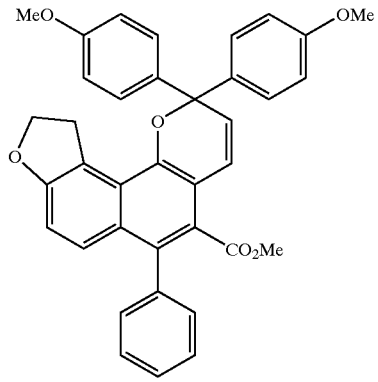

Proton NMR confirmed that Compound 1-5-p1 has the molecular structure of this example.

Comparative Example 2

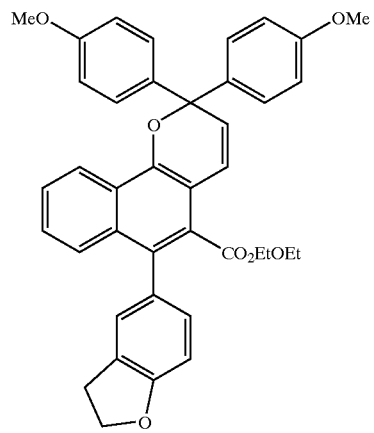

Proton NMR confirmed that Compound 1-5-p3 has the molecular structure of this example.

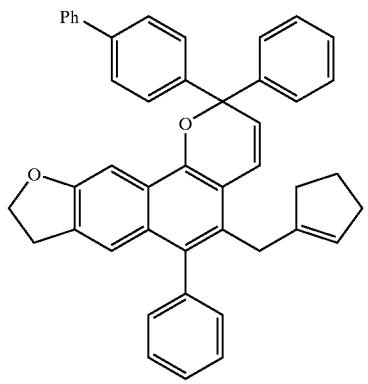

Example 2

Step 1: Compound 1-3-p1 from Step 3 of Example 1 (1.85 g) was mixed with 50 ml of methanol and 1 ml of concentrated HCl. The mixture was refluxed for 7 hours before it was cooled down to room temperature. 100 ml of water was then added. The product was extracted with 200 ml ether and followed by separation, drying over magnesium sulfate, filtering, and vacuum drying to yield 1.55 g of very light yellow powder.

Step 2: The product of Step 1 (0.5 g) was dissolved in 10 ml of THF, and 4 ml of cyclopentylmagnesium bromide (2M in ether) was dropped in at room temperature. After stirring for 2 days, few mililiters of 1N HCl was added in. The mixture was extracted with toluene, dried over magnesium sulfate, filtered, and concentrated to a solid paste. The paste was then washed with hexane to provide 0.64 g of off-white powder.

Step 3: The product from Step 2 (0.56 g) was mixed with 10 wt. % p-toluenesulfonic acid and 50 ml of toluene. The mixture was refluxed for one and half hour, concentrated, and chromatographied with silica column and 1:5 of EtOAc/Hexane as eluent. 0.08 g waxy solid was obtained.

Step 4: The waxy solid was then reacted with 1-phenyl-1-biphenyl-2-propyn-1-ol (0.1 g) in 15 ml of toluene and catalytic amount of p-toluenesulfonic acid for 30 minutes at 50 to 80° C. After concentrated and purified by a silica column with 1:15 ethyl acetate/hexane as eluent, the photochromic portion was re-crystallized in petroleum ether to yield 60 mg of light brown powder. Its structure was confirmed by NMR.

Example 3

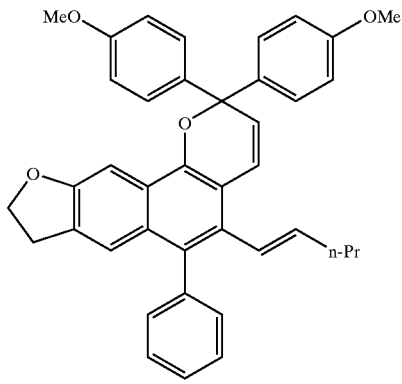

Step 1: Steps 2 and 3 of Example 2 were followed. except that cyclopentylmagesium bromide was replace by n-butylmagnesium chloride (3M in ether). In this case, two products were obtained as Compound 3-1-a (0.08 g) and 3-1-b (0.15 g). They are light yellow waxy solid.

Step 2: Compound 3-1-b (0.12 g) was reacted with 1,1-di(4-methoxyphenyl)-2-propyn-1-ol (0.24 g) in 20 ml of toluene and catalytic amount of p-toluenesulfonic acid for 50 minutes at 50 to 80° C. After concentrated and purified by a silica column with 1:20 ethyl acetate/hexane as eluent, 140 mg of white powder was obtained. Its structure was confirmed by NMR.

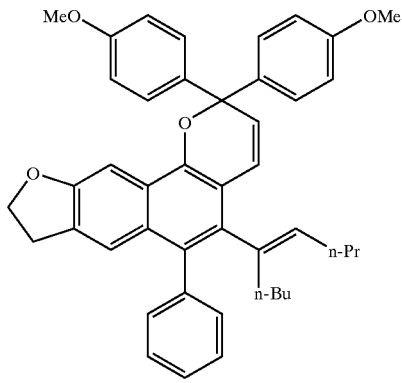

Example 4

Compound 3-1-a (0.08 g) was reacted with 1,1-di(4-methoxyphenyl)-2-propyn-1-ol (0.1 g) in 10 ml of toluene and catalytic amount of p-toluenesulfonic acid for 50 minutes at 30 to 80° C. After concentrated and purified by a silica column with 1:15 ethyl acetate/hexane as eluent, 80 mg of light yellow powder was obtained. Its structure was confirmed by NMR.

Photochromic Property Measurement:

Each of the compounds was dissolved in a solution of a thermoplastic polyurethane (20%) in THF to make a casting solution containing 1 wt. % of the photochromic compound with respect to the polyurethane. Photochromic polyurethane films of about 0.1 mm thick were then prepared with the casting solutions on flat borosilicate glass pieces. After complete evaporation of solvent, the UV-visible absorptions are then measured before and after exposure the photochromic polyurethane films to a 365 nm UV source. The photochromic properties: the wavelengths $\square_A$ and $\square_B$ of the two principle absorption bands and relative induced optical density (RIOD, defined as the ratio of induced optical density between band A and band B) of these compounds are given in the Table 1 below.

TABLE 1

| Compound | $\square_A$ (nm) | $\square_B$ (nm) | RIOD |
|---|---|---|---|
| Example 1 | 440 | 530 | 0.91 |
| Example 2 | 420 | 530 | 1.85 |
| Example 3 | 440 | 540 | 1.54 |
| Example 4 | 440 | 540 | 1.39 |
| Comparative Example 1 | 430 | 538 | 0.76 |
| Comparative Example 2 | 420 | 520 | 0.46 |

The data presented in Table 1 show that each tested compound of the present invention has two absorption peaks in the visible spectrum and a relative induced optical density of greater than 0.80. The data demonstrates that a single compound of the present invention exhibits a blended activated hue. By employing a compound of the present invention having two activated visible absorption maxima, fewer distinct compounds are required to achieve a blend of activated visible absorption maxima to produce the desired activated hue, e.g. neutral color. In addition, the blended activated hue of a compound of the present invention is particularly suitable for use in photochromic articles having a brown or driver activated color due to the greater optical density of Band A (420–500 nm) than the optical density of Band B (500–600 nm).

The present invention has been described with reference to specific details of particular embodiments thereof. It is not intended that such details be regarded as limitations upon the scope of the invention except insofar as to the extent that they are included in the accompanying claims. All publications and patents referred to in this application are hereby incorporated by reference.

What is claimed is:

1. A naphthopyran compound of the following formula:

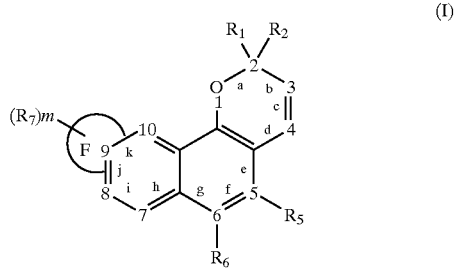

wherein (a) F is a 5- to 7-member saturated heterocyclic ring group fused to j side of the naphthopyran ring and containing an oxygen atom at the position adjacent to position 9;

(b) $R_6$ represents
   a hydrogen,
   a C1–C6 alkyl, alkoxy,
   a —C(O)R group, wherein R is selected from hydrogen, hydroxy, alkyl, alkoxy,
   an aryl or heteroaryl group which comprises in its basic structure (that is, in its ring atoms, the rings comprising 5, 6 or 7 atoms) 6 to 24 carbon atoms or 4 to 24 carbon atoms respectively and at least one heteroatom selected from sulfur, oxygen and nitrogen; the basic structure being optionally substituted with at least one substituent selected from:
a halogen atom (e.g., fluorine, chlorine and bromine),
a hydroxy group,
a linear or branched alkyl group comprising 1 to 12 carbon atoms,
a linear or branched alkoxy group comprising 1 to 12 carbon atoms,
a haloalkyl or haloalkoxy group corresponding to the (C1–C12) alkyl or alkoxy groups above respectively which are substituted with at least one halogen atom, and notably a fluoroalkyl group of this type,
a linear or branched alkenyl group comprising 2 to 12 carbon atoms, and notably a vinyl group or an allyl group,
an —$NH_2$ group,
an —$NHR_8$ group, $R_8$ representing a linear or branched alkyl group comprising 1 to 6 carbon atoms,
a

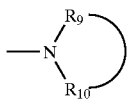

group, in which $R_9$ and $R_{10}$, which are the same or different, independently representing a linear or branched alkyl group comprising 1 to 6 carbon atoms, or representing (together with the nitrogen atom to which they are bound) a 5- to 7-membered ring which can comprise at least one other heteroatom selected from oxygen, sulfur and nitrogen, said nitrogen being optionally substituted with a group that is a linear or branched alkyl group comprising 1 to 6 carbon atoms,
a methacryloyl group or an acryloyl group,
a polyether, polyamide, polycarbonate, polycarbamate, polyurea or polyester residue;
(c) $R_5$ represents:
a hydroxy,
a halogen, and notably fluorine, chlorine or bromine,
a linear or branched alkyl group which comprises 1 to 12 carbon atoms (advantageously 1 to 6 carbon atoms),
a cycloalkyl group comprising 3 to 12 carbon atoms,
a linear or branched alkoxy group comprising 1 to 12 carbon atoms (most advantageously 1 to 6 carbon atoms),
a haloalkyl, halocycloalkyl, or haloalkoxy group corresponding to the alkyl, cycloalkyl, alkoxy groups above respectively, which are substituted with at least one halogen atom, notably selected from fluorine, chlorine and bromine,
a linear or branched alkenyl or alkynyl group comprising 1–12 carbon atoms, preferably a vinyl or allyl group,
a linear or branched alkenyloxy or alkynyloxy group comprising 1–12 carbon atoms, preferably an allyloxy group,
an aryl or heteroaryl group having the same definition as $R_6$ given supra,
an aralkyl or heteroaralkyl group, the alkyl group, which is linear or branched, comprising 1 to 4 carbon atoms, and the aryl and heteroaryl groups having the same definitions as R6 given supra,
an amine or amide group: —$NH_2$, —$NHR_8$, —$CONH_2$, —$CONHR_8$,

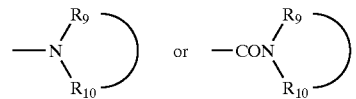

$R_8$, $R_9$, and $R_{10}$ having their respective definitions given above for the amine substituents of the values $R_6$,
a —$C(R_{11})_2X$ group, wherein X is —CN, halogen, hydroxy, alkoxy, benzoyloxy, C1–C6 acyloxy, amino, C1–C6 mono-alklamino, C1–C6 dialkyl amino, morpholino, piperidino, 1-indolinyl, pyrrolidyl, or trimethylsilyloxy, $R_{16}$ is hydrogen, C1–C6 alkyl, phenyl or naphthyl with C1–C6 alkyl or C1–C6 alkoxy substituents,
an —$OCOR_{12}$ or —$COOR_{12}$ group, $R_{12}$ representing a straight or branched alkyl group comprising 1 to 6 carbon atoms, or a cycloalkyl group comprising 3 to 7 carbon atoms, or a phenyl group, optionally substituted with at least one of the substituents listed above within the values in the definitions of $R_6$,
a methacryloyl group or an acryloyl group, an epoxy group having the formula,

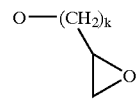

in which k=1, 2 or 3,
a polyether, polyamide, polycarbonate, polycarbamate, polyurea or polyester residue;
(d) $R_1$ and $R_2$, which are identical or different, independently represent:
a hydrogen,
a linear or branched alkyl group which comprises 1 to 12 carbon atoms (with or without substitution),
a cycloalkyl group which comprises 3 to 12 carbon atoms,
an aryl or heteroaryl group as $R_6$ defined supra,
an aralkyl or heteroaralkyl group, the alkyl group, which is linear or branched, comprising 1 to 4 carbon atoms and the aryl and heteroaryl groups having the definitions given above, or
the two substituents $R_1$ and $R_2$ together forming ring group such as those represented by an adamantyl, norbornyl, fluorenylidene, 5,5- or 10,10-di(C1–C6) alkylanthracenylidene, 5 (or 10)-(C1–C6)alkyl-5 (or 10)-OH (or $OR_{15}$)anthracenylidene or spiro(C5–C6) cycloalkylanthracenylidene ring group; said ring group being optionally substituted with at least one of the substituents listed above in the definitions for $R_1$, $R_2$; said ring group being optionally substituted with two adjacent groups that form a 5- to 6-member aromatic or non-aromatic ring which can comprise at least one heteroatom selected from oxygen, sulfur, and nitrogen;
(e) each $R_7$ group can be the same or different, independently representing
a hydrogen,
a linear, branched, or cyclic alkyl group,
a linear, branched, or cyclic alkoxy group,
a linear or branched alkenyl or alkynyl group,
a linear or branched alkenyloxy or alkynyloxy group,
an aryl or heteroaryl group having the same definition as that given supra for $R_6$,
two of the $R_7$ groups, which are adjacent or bonded to the same carbon atom in the group F, form a 5- to 7-membered non-aromatic ring which may have at least one hetroatom selected from the group consisting of oxygen, sulfur, and nitrogen, and m is an integer of 0 to 6.

2. The naphthopyran compound according to claim 1, wherein:

m is an integer of 1 or 2, $R'_1$ and $R'_2$, same or different, represent
  a hydrogen,
  a linear, branched, or cyclic alkyl,
  an alkyoxy with the alkyl portion being linear, branched, or cyclic,
  an unsubstituted, mono- or di-substituted aromatic group,
  an aryloxy with the aryl being unsubstituted, mono- or di-substituted;

$R_5$ represents
  a linear, branched, or cyclic alkyl group,
  a linear or branched alkenyl or alkynyl group,
  a —$C(R_{11})_2X$ group, wherein X is hydroxy, alkoxy, benzoyloxy, C1–C6 acyloxy,
  an optionally substituted phenyl or benzyl group,
  a —$COR_{12}$, or —$COOR_{12}$ group, $R_{12}$ representing a linear, branched, or cyclic alkyl group comprising 1 to 6 carbon atoms;

$R_6$ represents a unsubstituted, mono- or di-substituted aromatic or hetero-aromatic group selected from phenyl, naphthyl, pyridyl, furanyl, benzofuranyl, thenyl, benzothienyl;

$R_7$ represents
  a hydrogen,
  a linear, branched, or cyclic alkyl group,
  a linear, branched, or cyclic alkoxy group,
  a linear or branched alkenyl or alkynyl group,
  a linear or branched alkenyloxy or alkynyloxy group,
  an aryl or heteroaryl group having the same definition as that given supra for $R_6$,
  two of the $R_7$ groups, which are adjacent or bonded to the same carbon atom in the group F, form a 5- to 7-membered non-aromatic ring which may comprise at least one hetroatom selected from the group consisting of oxygen, sulfur, and nitrogen, and
  m is an integer of 0 to 2.

3. The naphthopyran compound according to claim 1, being further crosslinked.

4. The naphthopyran compound according to claim 1, being further polymerized.

5. A photochromic composition comprising:
  at least one compound according to claim 1;
  at least one linear or cross-linked (co)polymer which contains, in its structure, at least one compound according to claim 1;
  at least one additional photochromic compound of another type;
  at least one non-photochromic coloring agent; and
  at least one stabilizing agent.

6. The naphthopyran compound according to claim 1 being further incorporated into a (co)polymer matrix.

7. The naphthopyran composition according to claim 5 being further incorporated into a (co)polymer matrix.

8. A (co)polymer matrix comprising at least one co(polymer) and/or reticulate according to claim 4.

9. A (co)polymer matrix according to claim 6 further comprising one or more (co)polymer selected from the group consisting of: an alkyl, cycloalkyl, (poly or oligo) ethylene glycol or aryl or arylalkyl mono-, di-, tri-, or tetraacrylate or mono-, di-, tri-, or tetramethacrylate which is optionally halogenated or which optionally comprises at least one ether and/or ester and/or carbonate and/or carbamate and/or thiocarbamate and/or urea and/or amide group; polystyrene, polyether, polyester, polycarbonate, polycarbamate, polyepoxy, polyurea, polyurethane, polythiourethane, polysiloxane, polyacrylonitrile, polyamide, aliphatic or aromatic polyester, vinylic polymers, cellulose acetate, cellulose triacetate, cellulose acetate-propionate, polyvinylbutyral, poly(methyl methacrylate), poly(ethylene glycol bismethacrylate), poly(ethoxylated bisphenol A dimethacrylate), poly(vinyl acetate), polyvinylbutyral, polyurethane, polyanhydride and polymers of members of the group consisting of diethylene glycol bis(allyl carbonate) monomers, diethylene glycol dimethacrylate monomers, ethoxylated phenol bismethacrylate monomers, diisopropenyl benzene monomers and ethoxylated trimethylol propane triacrylate monomers.

10. The naphthopyran compound according to claim 1 being further incorporated into an ophthalmic lens.

11. The naphthopyran composition according to claim 5 being further incorporated into an ophthalmic lens.

12. The naphthopyran compound according to claim 3 being further incorporated into an ophthalmic lens.

13. The naphthopyran (co)polymer matrix according to claim 6 being further incorporated into an ophthalmic lens.

14. The naphthopyran (co)polymer matrix according to claim 9 being further incorporated into an ophthalmic lens.

15. A naphthopyran compound of the following formula:

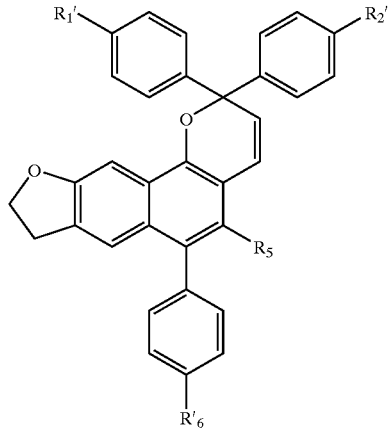

in which, $R'_1$, $R'_2$, and $R'_6$, same or different, represent
  a linear, branched, or cyclic alkyl group,
  an alkyoxy group with the alkyl portion being linear, branched, or cyclic;

$R_5$ represents
  a linear, branched, or cyclic alkyl group,
  a linear or branched alkenyl or alkynyl group,
  a —$C(R_{11})_2X$ group, wherein X is hydroxy, alkoxy, benzoyloxy, C1–C6 acyloxy, $R_{11}$ is hydrogen or C1–C6 alkyl;
  a substituted phenyl or benzyl group,
  a —$COR_{12}$, or —$COOR_{12}$ group, $R_{12}$ representing a linear, branched, or cyclic alkyl group having 1 to 6 carbon atoms, or a substituted phenyl or benzyl group.

* * * * *

UNITED STATES PATENT AND TRADEMARK OFFICE
CERTIFICATE OF CORRECTION

PATENT NO. : 6,963,003 B2 Page 1 of 1
DATED : November 8, 2005
INVENTOR(S) : Xuzhi Qin It is certified that error appears in the above-identified patent and that said Letters Patent is hereby corrected as shown below:

<u>Title page,</u>
Item [73], Assignee, delete "Vision-Ease Lane" and replace with -- Vision-Ease Lens --.

Signed and Sealed this

Twenty-eighth Day of March, 2006

JON W. DUDAS
*Director of the United States Patent and Trademark Office*